United States Patent
Dumousseaux

(10) Patent No.: US 8,133,508 B2
(45) Date of Patent: Mar. 13, 2012

(54) FLUORESCENT COSMETIC COMPOSITION

(75) Inventor: Christophe Dumousseaux, Tokyo (JP)

(73) Assignee: L'Oreal, Paris (FR)

(*) Notice: Subject to any disclaimer, the term of this patent is extended or adjusted under 35 U.S.C. 154(b) by 1332 days.

(21) Appl. No.: 11/540,651

(22) Filed: Oct. 2, 2006

(65) Prior Publication Data

US 2007/0077216 A1    Apr. 5, 2007

Related U.S. Application Data

(60) Provisional application No. 60/722,448, filed on Oct. 3, 2005.

(51) Int. Cl.
*A61K 9/14* (2006.01)
*A61K 8/00* (2006.01)

(52) U.S. Cl. ........ 424/484; 424/489; 424/70.1; 424/424

(58) Field of Classification Search .................. 424/484, 424/489, 70.1, 424
See application file for complete search history.

(56) References Cited

U.S. PATENT DOCUMENTS

| | | | |
|---|---|---|---|
| 6,586,013 B2 | 7/2003 | Victor | |
| 6,749,777 B2 * | 6/2004 | Argoitia et al. | 252/582 |
| 7,264,670 B2 * | 9/2007 | Ruger et al. | 106/404 |
| 2006/0251687 A1 * | 11/2006 | Lapidot et al. | 424/401 |

FOREIGN PATENT DOCUMENTS

| | | |
|---|---|---|
| JP | A 02-295912 | 12/1990 |
| JP | A 06-047273 | 2/1994 |
| JP | A 08-239310 | 9/1996 |
| WO | WO 2004/081222 A2 | 9/2004 |
| WO | WO 2005/009604 A1 | 2/2005 |
| WO | WO 2005/011622 A1 | 2/2005 |

OTHER PUBLICATIONS

European Search Report in European Patent Appln No. 06 30 1006, mailed Jan. 10, 2007.
Written Opinion of European Examiner in European Patent Appln No. 06 30 1006 with English-language translation, mailed Jun. 29, 2007.

* cited by examiner

*Primary Examiner* — Gina C Yu
(74) *Attorney, Agent, or Firm* — Oliff & Berridge, PLC

(57) ABSTRACT

The present invention relates to a cosmetic composition containing, in a physiologically acceptable medium, fluorescent particles comprising molecules of at least one fluorescent organic compound trapped inside a matrix at least partially formed by at least one metal oxide, said composition comprising less than 100 mg/l of said fluorescent organic compound or compounds dissolved in a liquid phase of the medium.

17 Claims, No Drawings

FLUORESCENT COSMETIC COMPOSITION

This non provisional application claims the benefit of U.S. Provisional Application No. 60/722,448 filed on Oct. 3, 2005.

The present invention relates to a cosmetic composition for application to keratinous substances, for example the skin, hair, lips, nails, or eyelashes.

BACKGROUND

Fluorescent pigments or colorants are very important to the cosmetics industry. They can produce very brilliant, very lively colors which cannot be produced with conventional coloring substances. When they do not absorb in the visible region, they can also lighten and significantly enhance the reflectance of substrates onto which they are deposited, such as the skin and hair.

Of the various available fluorescent materials, the skilled person will be aware that fluorescent organic molecules are the most effective as regards intensity of fluorescence. Their use can produce highly fluorescent compositions containing a small quantity of fluorescent agent.

Said organic molecules are, however, difficult to formulate as they are generally soluble in a very limited number of solvents. Their intensity of fluorescence also depends greatly on the solvent used in the formulation and they are strongly fluorescent in only a small number of solvents. Thus, they are of limited possible use in cosmetic formulations. They may also present problems with safety when they come into contact with keratinous substances.

In order to overcome those disadvantages, the encapsulation of organic molecules in various organic matrices (U.S. Pat. No. 6,586,013) or inorganic matrices (Japanese patent JP-06-47273 and JP-08-239310) has been envisaged. However, all of the matrices used until now are porous to a certain extent and allow the molecule to diffuse outwardly. That molecule can thus find its way into the continuous liquid medium of the formulation, which may result in contact with the keratinous substances.

SUMMARY

The invention provides, according one of its aspects, a cosmetic composition containing in a physiologically acceptable medium, fluorescent particles comprising molecules of at least one fluorescent organic compound trapped inside a matrix at least partially formed by at least one metal oxide, said composition comprising less than 100 mg/l of said fluorescent organic compound or compounds dissolved in a liquid phase of the medium.

The cosmetic composition may comprise less than 50 mg/l of said fluorescent organic compound or compounds dissolved in said liquid phase.

In another embodiment, the cosmetic composition may comprise less than 10 mg/l of said fluorescent organic compound or compounds dissolved in said liquid phase.

The invention also provides, in one of its aspects, a cosmetic composition in a physiologically acceptable medium, fluorescent particles comprising molecules of at least one fluorescent inorganic compound encapsulated within a matrix at least partially formed by at least one metal oxide and comprising organic groups, for example phenyl or alkyl, which can create interactions, for example via Van der Waals forces or hydrogen bonds, with the fluorescent organic molecules.

The invention also provides a cosmetic composition containing, in a physiologically acceptable medium, fluorescent particles comprising molecules of at least one fluorescent inorganic compound encapsulated within a matrix at least partially formed by at least one metal oxid and comprising organic groups, for example phenyl or alkyl, which can create interactions such as Van der Waals forces or hydrogen bonds, with the fluorescent organic molecules.

The invention also provides a physiologically acceptable medium, fluorescent particles comprising molecules of at least one fluorescent organic compound trapped inside a non-porous matrix at least partially formed by at least one metal oxide.

In one of the aspects of the invention, it fluorescent organic molecules may be used in an effective and safe manner by encapsulating them hermetically in a non-porous matrix formed by at least one metal oxide, while retaining their fluorescent properties.

The particles obtained, when introduced into a cosmetic composition, can endow with fluorescent properties thereon.

Advantageously, the matrix also includes a small proportion of organic groups such as phenyl or alkyl groups. The function of said organic groups is to create an interaction, for example via Van der Waals forces or hydrogen bonds, with the fluorescent organic molecules to limit their discharge into the medium of the formulation.

According to a further aspect of the invention, discharge of the organic molecules may be further limited by increasing the density of the network of metal oxides, by adding thereto a small proportion of at least one inorganic substance, for example phosphorus in the form of a phosphoric acid or ester, which can create bi- or tri-functional bridges with the metal oxides.

The fluorescent organic molecules may have different chemical natures and may or may not be colored. For example, molecules of the fluorescein, pyrazine, coumarin, naphthalimide, triazine, dioxazine, sulforhodamine, azo compound, azomethinic compound, stilbene derivative, oxazole derivative, benzoxazole, or imidazole families can be cited.

The fluorescent molecules may be hydrosoluble, liposoluble, or soluble in other solvents such as alcohols.

The fluorescent molecules of the invention are preferably completely or partially hydrosoluble, i.e. soluble in water at a concentration of at least 1 mg/l [milligram per liter] preferably at least 10 mg/l.

The non-colored molecule may be an optical whitening agent absorbing light between 300 nm [nanometers] and 400 nm and emitting light between 400 nm and 700 nm, preferably between 400 nm and 500 nm. Such optical whitening agents are commercially available from Ciba Specialty Chemicals from the Uvitex® or Tinopal® range, from CLARIANT from the Leucophor® range, from Bayer Chemicals from the Blankophor® range or from BASF from the Ultraphor® range.

Preferred colored molecules which may be used are the following as listed by the FDA: D&C Yellow 7, 8, 10, 11, D&C Red 3, 21, 322, 27, 28, D&C Green 5, 6, 8, D&C Orange 5, D&C Violet 2, and ext D&C Violet 2.

In accordance with an exemplary implementation, the matrix is produced by sol-gel synthesis from a metal oxide in the presence of acid, ester, or phosphoric salt, followed by drying at a temperature in the range 80° C. to 200° C. In practice, it is possible to use phosphoric acid or calcium, magnesium, or sodium phosphate. Phosphoric acid, $H_3PO_4$, is preferred. Its presence allows a very dense network to be formed during condensation of the metal oxide, in particular by forming phosphate bridges. Its concentration may be in the range 0.01% to 0.25% relative to the total weight of the matrix. The metal alkoxide is preferably selected from silicon, titanium, aluminum, or zirconium alkoxides. To obtain a transparent matrix, a silicon alkoxide is preferably used. Said silicon alkoxide contains at least one Si(OR) group in which the organic group R is preferably an alkyl chain containing 1 to 5 carbon atoms.

The inorganic matrix of particles used in the compositions of the invention is insoluble in the continuous medium of the formulation. The particles are thus insensitive to the solvents and to temperature conditions.

The terms "non porous matrix" advantageously mean that less than 2%, preferably less than 1% and more preferably less than 0.5% by weight of the fluorescent organic molecules contained in the matrix has discharged after the particles containing them have been left for at least one hour in the liquid phase in which said molecules are soluble. The liquid phase is at a temperature of 25° C. The concentration of the particles in the medium is 1% by weight relative to the weight of the liquid phase.

With such discharge-free properties and in another aspect of the invention, the liquid phase in which the fluorescent molecules are soluble preferably contains less than 100 mg/l of fluorescent organic molecules dissolved in the continuous medium, preferably less than 50 mg/l and more preferably less than 10 mg/l.

The absorption of oil from the particles used in the compositions of the invention is preferably very low. Typically, it is in the range 10 ml/100 g [milliliters per 100 grams] to 100 ml/100 g, preferably in the range 20 ml/100 g to 60 ml/100 g.

The concentration of fluorescent molecules in the particles may be in the range 0.01% to 50% by weight, preferably in the range 0.1% to 20% by weight, more preferably in the range 0.5% to 5%.

The particles may contain a mixture of a plurality of fluorescent organic molecules. They may also contain other compounds which may optionally be fluorescent (fluorescent inorganic nanoparticles or nanoparticles of metal oxides, for example).

The particles may be present in the compositions of the invention at a concentration in the range 0.5% to 95%, preferably in the range 1% to 70%, more preferably in the range 5% to 30%.

Additional Compounds

The compositions of the invention may contain one or more additional compounds selected from those described in the Applicant's U.S. patent application No. 60/554,929 filed on 22 Mar. 2004, the content of which is incorporated herein by reference.

The composition according to the invention may also contain ingredients commonly used in cosmetics, such as vitamins, thickeners, trace elements, softeners, sequestering agents, fragrances, acidifying or basifying agents, preserving agents, sunscreens, surfactants, antioxidants, agents for preventing hair loss, antidandruff agents and propellants, or mixtures thereof.

Needless to say, a person skilled in the art will take care to select this or these optional additional compound(s), and/or the amount thereof, such that the advantageous properties of the corresponding composition according to the invention are not, or are not substantially, adversely affected by the envisaged addition.

A person skilled in the art will be able to select the appropriate galenical form, and also the method for preparing it, on the basis of his general knowledge, taking into account firstly the nature of the constituents used, especially their solubility in the support, and secondly the intended application of the composition.

Packaging and/or Applicator Devices

The composition may be packaged in multiple forms, with or without an applicator, depending on its dosage form.

The composition may be packaged in a packaging device such as a box, receptacle, or case, that is leaktight, at least before first use. The packaging device may be made at least in part using a thermoplastic material, or in a variant without using any thermoplastic material. The packaging device may comprise a polyolefin. The packaging device may also include at least one metal element, e.g. a cup, a twisted metal core, a hinge, a ring, or a cover.

When the composition is for application by means of an applicator, the applicator may comprise, for example, a foam, an optionally flocked endpiece, a felt, a brush, a comb, a paintbrush, or a piece of woven or non-woven fabric.

The composition may also impregnate a substrate, e.g. a paper, or a woven or non-woven fabric.

When present, the applicator may be received removably on the packaging device containing the composition. In a variant, the applicator may be permanently secured to the packaging device containing the composition. The packaging device may comprise a piston or any other means for enabling the applicator to be fed with the composition.

The packaging device may comprise a dispenser member such as a pump or a valve, for example when the composition is liquid.

When present, the applicator may comprise a stem connected to a member for closing the packaging device, which closure member may also constitute a handle member, where appropriate.

The closure device containing the composition may be provided with a catch or any other fastener means, e.g. magnetic means or snap-fastener means.

The packaging device may also be provided with fastener means engaged by screw-fastening, friction or snap-fastening.

The packaging device may comprise sealing means such as, for example: an annular sealing lip or an elastomer gasket, either injection-molded onto the device or fitted thereto.

The packaging device containing the composition may carry a label or printing, e.g. showing a trademark or a logo, with the printing being performed, for example, by hot- or cold-transfer or by silkscreen printing or by some other printing technique.

The packaging device containing the composition may comprise a card package or a blister pack, e.g. being made in part out of transparent plastics material.

Makeup Method

The invention also provides a method of applying makeup and/or a non-therapeutic care product to the skin, the lips, and/or keratinous fibers, the method comprising applying a composition as defined above to the skin, the lips, and/or keratinous fibers. Before performing the application, a measurement of optical properties may be performed in order to formulate the composition accordingly.

Physiologically Acceptable Medium

The composition of the invention comprises at least one physiologically acceptable medium.

The terms "physiologically acceptable medium" are synonymous of "cosmetically medium" and are used to designate a medium that is not toxic and that is suitable for application to the skin, to the lips, or to keratinous material of human beings. The physiologically acceptable medium is generally adapted to the nature of the substrate onto which the composition is to be applied and also on the way in which the composition is to be packaged.

In exemplary embodiments, the composition of the invention may comprise a fatty phase, for example comprising 5% to 80% by weight, or 5% to 50% by weight relative to the total weight of the composition.

Oils that may be used in the composition may be selected from those conventionally used in the cosmetic field.

The composition may include an oil, for example an oil selected from:
- hydrocarbon oils of animal origin, such as perhydrosqualene;
- hydrocarbon oils of vegetable origin, such as liquid triglycerides of fatty acids having 4 to 10 carbon atoms, and the liquid fraction of shea butter;
- synthesized ethers and esters, in particular of fatty acids, such as oils having formulae $R^1COOR^2$ and $R^1OR^2$ where $R^1$ represents the residue of a fatty acid or a fatty alcohol having 8 to 28 carbon atoms, and $R^2$ represents an optionally branching hydrocarbon chain containing 3 to 30 carbon atoms, such as, for example, Purcellin oil, isononyl isononanoate, isopropyl myristate, ethyl-2-hexyl palmitate, octyl-2-dodecyl stearate, octyl-2-docecyl erucate, isostearyl isostearate; hydroxyl esters such as isostearyl lactate, octylhydroxystearate, octyldocecyl hydroxystearate, diisotearyl malate, triisocetyl citrate, hepatanoates, octanoates, decanoates of fatty alcohols; polyol esters such as propylene glycol dioctanoate, neopentylglycol diheptaonoate, and diethyleneglycol diisononanoate; and esters of pentaerythritol such as pentaerythrityl tetraisostearate;
- linear or branching hydrocarbons of mineral or synthetic origin, such as optionally volatile paraffin oils and derivatives thereof, Vaseline, polydecenes, hydrogenated polyisobutene such as parleam oil;
- fatty alcohols having 8 to 26 carbon atoms, such as cetylic alcohol, stearylic alcohol, and mixtures thereof (cetyl-stearylic alcohol), octyldodecanol, 2-butyloctanol, 2-hexyldecanol, 2-undecylpentadecanol, oleic alcohol, or linoleic alcohol;
- partially hydrocarbon and/or silicone fluorinated oils such as those described in document JP-A-2-295 912;
- silicone oils such as optionally volatile polymethylsiloxanes (PDMS) having a linear or cyclic silicone chain, that are liquid or pasty at ambient temperature, for example cyclopolydimethylsiloxanes (cylmethicones) such as cyclohexasiloxane; polydimethylsiloxanes having alkyl, alcoxy, or phenyl groups, either pendant or at the end of the silicone chain, the groups having 2 to 24 carbon atoms; phenyl silicones such as phenyltrimethicones, phenyldimethicones, phenyltrimethylsiloxy-diphenyl-siloxanes, diphenyl-dimethicones, diphenyl-methyldiphenyl trisiloxanes, 2-phenylethyltrimethylsiloxysilicates, and polymethylphenylsiloxanes; and mixtures thereof.

When the composition is in the form of an emulsion having a fatty phase, it may also comprise an emulsifier, and optionally a coemulsifier.

As examples of emulsifiers and coemulsifiers suitable for use in the invention, mention can be made of O/W emulsifiers such as fatty acid esters and polyethylene glycol, for example PEG-100 stearate, and fatty acid esters and glycerine such as glyceryl stearate, and also W/O emulsifiers such as oxyethylene poly(methylcetyl)(dimethyl)methylsiloxane available under the commercial name Abi WE09 from the supplier Degussa Goldschmidt or the mixture of ethylene glycol acetyl stearate and glyceryl tristearate sold by the supplier Guardian under the trade name Unitwix. Mention can be also made of emulsifying silicone elastomer as described previously.

The emulsifier and optionally the coemulsifier are generally present in the composition at a proportion lying in the range 0.3% to 30% by weight, and for example lying in the range 0.5% to 20% by weight relative to the total weight of the composition.

The composition of the invention may also comprise at least one wax, at least one gum, and at least one pasty fatty substance of vegetable, animal, mineral, or synthetic origin, optionally treated with silicone.

The waxes may be hydrocarbon, silicone, and/or fluorinated waxes, optionally made up of ester or hydroxyl functions. They may be of natural origin.

The wax may represent 0.01% to 10% by weight, or 0.1% to 5% by weight relative to the total weight of the composition. In an embodiment, the composition may be free of any wax.

The composition may also comprise at least one optionally coated organic or inorganic filler, for example as an anti-shine agent, for example zinc and zirconium oxide, silica, alumina, boron nitride, talc, sericite, mica, clays, starch and derivatives thereof, for example the starch cross-linked with octenylsuccincic anhydride and sold by the supplier National Starch under the name DRY FLO PLUS (28-1160), aqueous dispersions of acrylic styrene, particles of melamine-formaldehyde or urea-formaldehyde resin, aqueous dispersions of polytetrafluoroethylene, microdispersions of waxes, copolymers of vinylpyrrolidone and 1-triacontene, hydrodispersible polymers containing LCST units, silicone resins and waxes, for example microbeads of silicone resin such as those sold under the name TOSPEARL by the supplier Toshiba Silicone, expanded powders such as hollow microspheres and for example the microspheres sold under the name EXPANCEL by the supplier Kemanord Plast or under the name MICROPEARL F 80 ED by the supplier Matsumoto, microspheres of expanded vinylidene chloride, acrylonitrile, and methacrylate terpolymer, polyamide particles, e.g. Nylon® particles or those sold under the name ORGASOL by the supplier Atochem, microbeads of cellulose, fibers, powers of polyethylene, microspheres based on acrylic copolymers such as microspheres of ethylene glycol dimethacrylate and lauryl methacrylate copolymer sold by the supplier Dow Corning under the name POLYTRAP, and mixtures thereof.

The filler, when used as an anti-shine agent, may be present at a concentration lying in the range 0.1% to 80% by weight relative to the total weight of the composition, for example a concentration lying in the range 0.1% to 10% by weight relative to the total weight of the composition.

Naturally, the anti-shine agent and the quantity of agent used should be selected by the person skilled in the art so as to avoid deteriorating the looked-for properties.

The composition may also contain at least one additive that is conventional in the field of cosmetics, such as fillers, e.g. selected from the above list, hydrophilic or lipophilic gelling agents, hydrosoluble or liposoluble agents, preservatives, hydrating agents such as polyols and for example glycerin, sequestering agents, antioxidants, solvents, fragrances, physical and chemical sun filters, for example against UVA and/or UVB, odor absorbers, (acidic or basic) pH adjusters, and mixtures thereof.

The quantities of these various additives are those conventionally used in the field in question, for example 0.01% to 20% of the total weight of the composition.

In any event, the additives, and the proportions thereof, should be selected in such a manner as to avoid degrading the properties looked for in the invention.

As active agents, mention can be made in particular of the following:

- agents known for their activity on aging of the skin such as keratolytic and peeling-enhancing agents, e.g. α-hydroxy acids, β-hydroxy acids, α-aceto acids, β-aceto acids, retinoids and esters thereof, retinal, retinoic acid, and derivatives thereof;
- vitamins, such as for example vitamins A, B3, PP, B5, E, K1 and/or C, and derivatives of said vitamins, and for example their esters;
- free radical scavengers;
- sun filters;
- hydrating agents such as polyols;
- ceramides;
- DHEA and derivatives thereof;
- the coenzyme Q10;
- dipigmenting and lightening agents acting in complementary biological manner such as kojic acid, extracts of scutellaria, mulberry, licorice, and/or camomile, derivatives of para-aminophenols, arbutine and derivatives thereof, and mixtures thereof;
- agents suitable for use on fatty or mixed skin, such as salts of zinc, and for example zinc oxide and zinc gluconate;
- antibacterial agents such as salicylic acid and derivatives thereof such as n-octanoyl-5-salicylic acid, triclosan, lipacid, capryloylglycine, clove extract, octopirox, hexamidine, azelaic acid, and derivatives thereof;
- anti-acne agents, or indeed;
- extracts from phlebotonic plants such as extracts of ruscus and/or horse chestnut; xanthic bases such a caffeine.

The composition of the invention may be presented in any of the dosage forms used in the field of cosmetics, and normally used for topical application: direct, inverse, or multiple emulsions; gels; creams; solutions; suspensions; lotions; free powders; compacts; and sticks.

More precisely, it may be in the form of an optionally gelled oily solution of an emulsion having a liquid or semi-liquid consistency of the lotion type obtained by dispersing a fatty phase in an aqueous phase (O/W) or conversely an aqueous phase in a fatty phase (W/O), a triple emulsion (W/O/W/ or O/W/O), or a suspension or an emulsion of soft, semi-solid, or solid consistency of the cream or gel type, or indeed microemulsions, microcapsules, microparticles, or a vesicular dispersion of ionic type (liposomes or oleosomes) and/or of non-ionic type (niosomes) and/or a dispersion of nanocapsules or nanospheres.

The cosmetic composition of the invention may be presented in the form of a skin-care, makeup, and/or sunscreen composition.

The composition of the invention may be in the form of makeup for the face, for example the skin and/or the lips, e.g. in the form of a foundation.

The composition of the invention may also be in the form of a skin-care and/or makeup composition for the skin, the lips, and/or keratinous fibers.

For example, the composition may be in the form of a concealer gel, a skin-care cream, or a photoprotective lotion, for example against UV.

EXAMPLES

The proportions are in weight except if the contrary is specified.

Example 1

Synthesis of a Matrix Containing a Fluorescent Molecule

Firstly, 60 g [grams] of isopropanol, 57.5 g of tetramethoxysilane (TMOS) and 0.6 g of Tinopal CBX (an optical whitening agent sold by Ciba Specialty Chemicals) were mixed, then 102 g of 0.01N phosphoric acid (0.005 mole/l) was added and it was stirred for 24 h at 25° C. to obtain a sol.

Next, the sol was applied to a steel plate using a spin-coater (rotation rate 600 rpm [revolutions per minute]) to form a film, left for 30 s [seconds] at ambient temperature then dried at 200° C. for 60 s. The film obtained was broken to obtain platelets with a thickness of 1 μm [micrometer] and a mean size of 5 μm to 50 μm. These particles contained 2.5% by weight of Tinopal CBX and were white in color.

These particles fluoresced strongly with an emission maximum at 440 nm.

Example 2 and Comparative Examples 3 and 4

The following formulations were produced:

|  | Example 2 | Example 3 (comparative) | Example 4 (comparative) |
|---|---|---|---|
| Ultrapure water | 99 | 99 | 99 |
| Particles of Example 1 | 1 |  |  |
| Dermaglo DG-00[1] |  | 1 |  |
| Colment Crazy Blue Azur[2] |  |  | 1 |
| Quantity of Tinopal CBX present in aqueous solution (mg/l) after one hour at temperature of 25° C. | 0.5 | 147 | 250 |

[1]particles of polyester containing 3% Tinopal CBX sold by Dayglo
[2]particles of PMMA containing 2.5% of Tinopal CBX sold by LCW To measure the quantity of Tinopal CBX present in the aqueous solution outside the particles, we used the following procedure: the solutions were centrifuged for 1 h[hours] at 4000 rpm, then the supernatant was taken and centrifuged again for 1 h [hour] at 4000 rpm. The final supernatant was diluted by a factor of 10 with ultrapure water and the fluorescent intensity was measured using a JASCO FP6000 spectrofluorimeter. The concentration was then determined by comparison with a calibration curve for Tinopal CBX in aqueous solution.

Example 5

Liquid Foundation

| Phase I | |
|---|---|
| Cetyl dimethicone copolyol/polyglyceryl-4 isostearate/hexyl laurate | 8 g |
| Dimethicone | 4.8 g |
| Cyclomethicone | 5.2 g |
| Isododecane | 2.8 g |
| Isostearyl neopentanoate | 0.8 g |
| Bentone gel | 8 g |
| Titanium dioxide | 5 g |
| Iron oxide | 1 g |

-continued

| Phase II | |
|---|---|
| Water | 43.2 g |
| Butylene glycol | 5.6 g |
| Magnesium sulfate | 0.8 g |
| Preservatives | 0.8 g |
| Phase III | |
| Talc | 4 g |
| Particles of Example 1 | 10 g |

Phases I and II were mixed separately, phase II was added to phase I using a suitable turbine to achieve emulsification. Phase III was then added to the emulsion.

Example 6

Nail Polish

| Nitrocellulose | 20 g |
|---|---|
| N-ethyl sulfonamide o, p-toluene | 6 g |
| Tributyl acetyl citrate | 6 g |
| Hectorite | 1 g |
| Particles from Example 1 | 10 g |
| Isopropanol | 8 g |
| Ethyl acetate/butyl acetate | quantity sufficient for 100 g |

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A cosmetic composition containing, in a physiologically acceptable medium, fluorescent particles comprising molecules of at least one fluorescent organic compound encapsulated inside a matrix at least partially constituted by at least one metal oxide and at least one bi-, tri-, tetra- or penta-valent inorganic element.

2. A cosmetic composition according to claim 1, wherein the inorganic element is phosphorus.

3. A cosmetic composition containing, in a physiologically acceptable medium, fluorescent particles comprising molecules of at least one fluorescent organic compound encapsulated inside a non-porous matrix at least partially constituted by at least one metal oxide,
wherein the fluorescent particles are platelet-shaped wherein the non-porous matrix comprises a metal oxide network, and
wherein the fluorescent organic compound is encapsulated within the metal oxide network.

4. A cosmetic composition according to claim 1, wherein the fluorescent organic compound or compounds are selected from fluoresceins, pyrazines, coumarins, naphthalimides, triazines, dioxazines, sulforhodamines, azo compounds, azomethinic compounds, stilbene derivatives, oxazole derivatives, benzoxazole, imidazole and mixtures thereof.

5. A cosmetic composition according to claim 1, wherein the metal oxide or oxides are selected from oxides of silicon, titanium, aluminum, zirconium and mixtures thereof.

6. A cosmetic composition according to claim 5, wherein the metal oxide or oxides are selected from oxides of silicon.

7. A cosmetic composition according to claim 1, wherein the physiologically acceptable medium includes a liquid phase that contains at least one volatile solvent.

8. A cosmetic composition according to claim 1, wherein said fluorescent particles are present in an amount of 0.5% to 95% by weight, with respect to the total composition weight.

9. A cosmetic composition according to claim 1, wherein said fluorescent particles are present in an amount of 1% to 70% by weight with respect to the total composition weight.

10. A cosmetic composition according to claim 1, wherein said fluorescent particles are present in an amount of 5% to 30% by weight with respect to the total composition weight.

11. A cosmetic composition according to claim 1, comprising at least one additional coloring substance selected from titanium dioxide and zinc oxide.

12. A cosmetic composition according to claim 1, further comprising at least one additional powdered substance selected from talc, mica, silica, polyamide and polymethylmethacrylate.

13. A cosmetic composition according to claim 1, wherein said fluorescent particles have a mean size by volume of 0.1 μm to 50 μm.

14. A cosmetic composition according to claim 1, wherein said fluorescent particles have a mean size by volume of 0.5 μm to 20 μm.

15. A method for making up and/or caring for keratinous substances, comprising applying thereto a cosmetic composition according to claim 1.

16. A method according to claim 15, wherein the keratinous substances are selected from eyelashes, nails, skin, hair and lips.

17. A cosmetic composition according to claim 7, wherein the solvent comprises at least one member selected from the group consisting of water, an alcohol and an oil.

* * * * *